United States Patent
Yeganeh

(10) Patent No.: US 9,480,984 B2
(45) Date of Patent: Nov. 1, 2016

(54) DEVICE FOR STANDARD PREPARATION OF URINARY SEDIMENT FOR URINE ANALYSIS (MONO SYSTEM)

(71) Applicant: Morteza Norouzi Yeganeh, Karaj (IR)

(72) Inventor: Morteza Norouzi Yeganeh, Karaj (IR)

( * ) Notice: Subject to any disclaimer, the term of this patent is extended or adjusted under 35 U.S.C. 154(b) by 54 days.

(21) Appl. No.: 14/450,180

(22) Filed: Aug. 1, 2014

(65) Prior Publication Data

US 2016/0030940 A1    Feb. 4, 2016

(51) Int. Cl.
*B01L 3/00*    (2006.01)

(52) U.S. Cl.
CPC ............... *B01L 3/561* (2013.01); *B01L 3/502* (2013.01); *B01L 2200/0605* (2013.01); *B01L 2300/046* (2013.01); *B01L 2300/0832* (2013.01); *B01L 2300/0861* (2013.01); *B01L 2400/0457* (2013.01)

(58) Field of Classification Search
CPC .... B01L 3/561; B01L 3/502; B01L 17/0208; B01L 21/00; B01L 43/00; B01L 49/003; B65D 1/323; B65D 47/06
USPC ............................................. 422/523; 73/421
See application file for complete search history.

(56) References Cited

U.S. PATENT DOCUMENTS

| | | | | |
|---|---|---|---|---|
| 2,198,256 A | * | 4/1940 | Levy | B01L 3/5021 241/DIG. 30 |
| 3,618,392 A | * | 11/1971 | Echols | B01L 3/02 356/246 |
| 3,813,223 A | * | 5/1974 | Fleck | B01L 3/50825 422/550 |
| 4,024,857 A | * | 5/1977 | Blecher | A61B 5/1411 422/419 |
| 2014/0076937 A1 | * | 3/2014 | Cavalier | B65D 47/265 222/481 |

OTHER PUBLICATIONS

Ben-Ezra J et al. Basic examination of Urine IN: McPherson RA, Pincus MR. Henry's clinical Diagnosis and Management by Laboratory Methods. 21st edition. Philadelphia, PA. Saunders Elsevier, 2007, p. 419.
Linne and Ringsrud's clinical laboratory science. 5th ed, 2007; p. 385.
Barbara H, Anna P, Reynolds, Norma J, Walters, Basic clinical laboratory techniques, 5th ed. 2008, p. 488.

* cited by examiner

*Primary Examiner* — Jill Warden
*Assistant Examiner* — Jacqueline Brazin
(74) *Attorney, Agent, or Firm* — Azadeh Saidi

(57) ABSTRACT

A System for use in sample processing for urine sediment analysis that is composed of a main tube and a thinner inner tube (without capillarity), which is attached to the wall of the main tube and has the volume equal to one twelfth of the main tube. Near an upper end of both tubes, a small connected aperture on each tube allows evacuation of air from the inner tube when urine enters this tube from an open end. After urine centrifugation, the small opening is closed by operator's finger and the supernatant is poured out from the main tube. This allows retention of the urine in the inner tube, which will be added to the sediment after unblocking of the aperture.

15 Claims, 7 Drawing Sheets

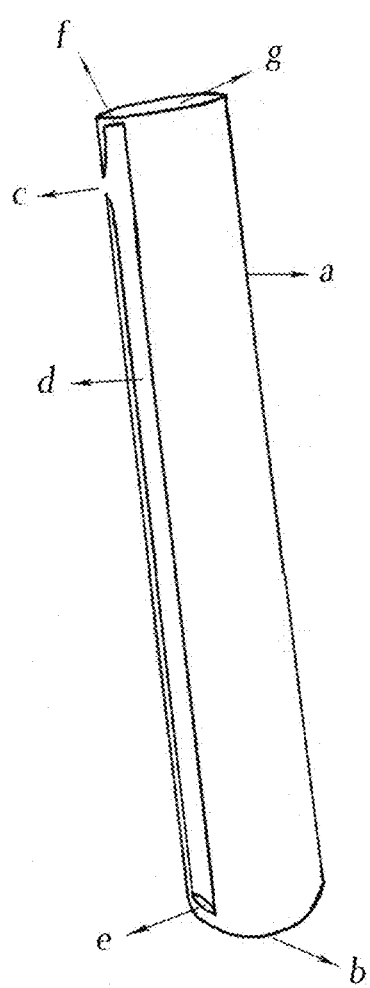
Fig. 1.I

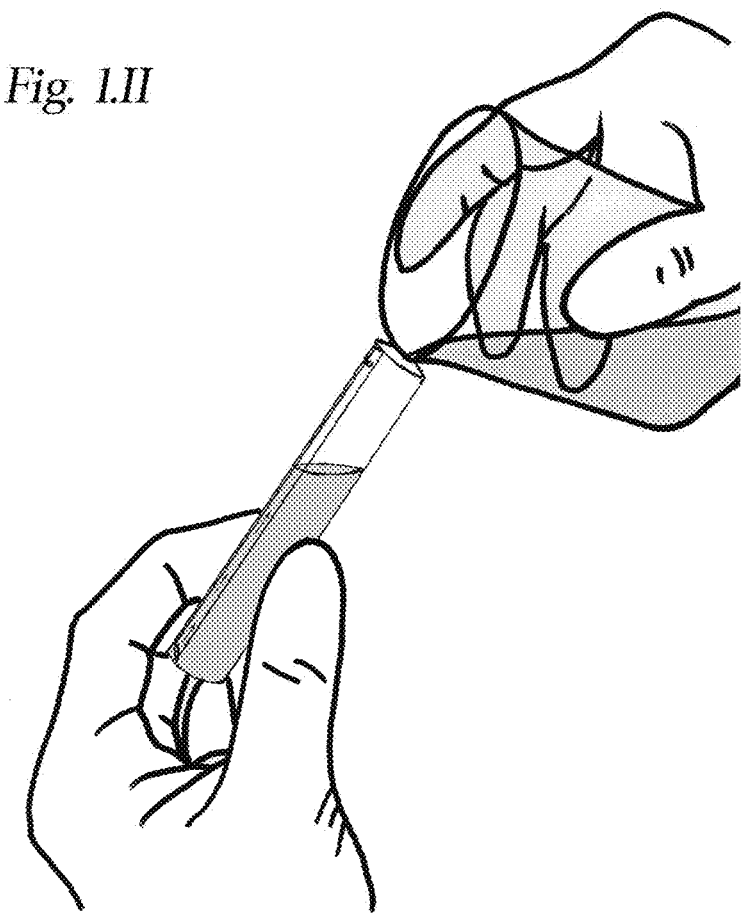
Fig. 1.II

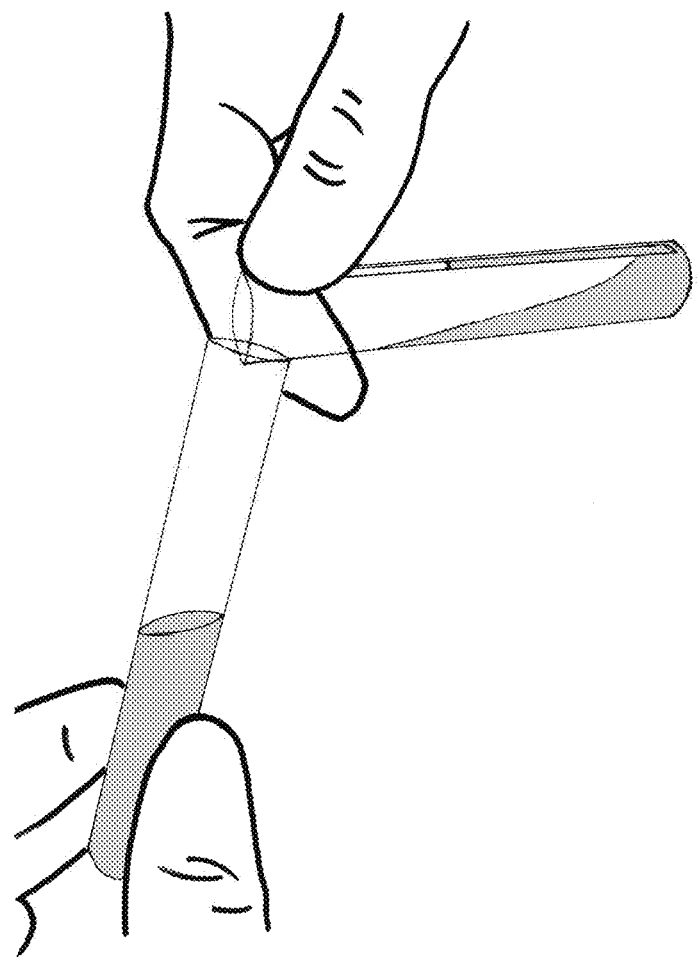
Fig. 1.III

Fig. 3
Fig. 4
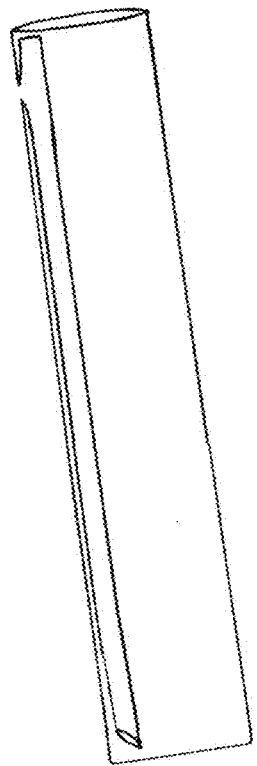
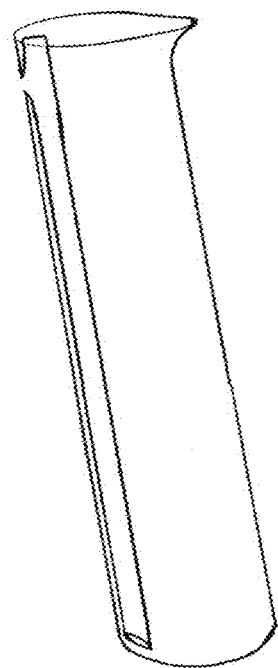

Fig. 5
Fig. 6.I
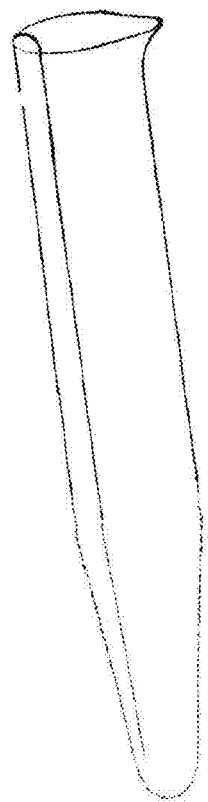
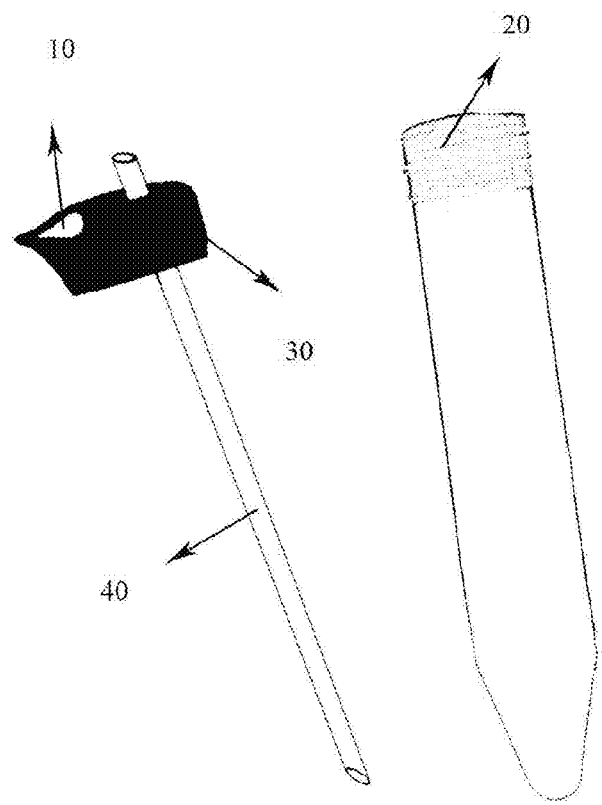

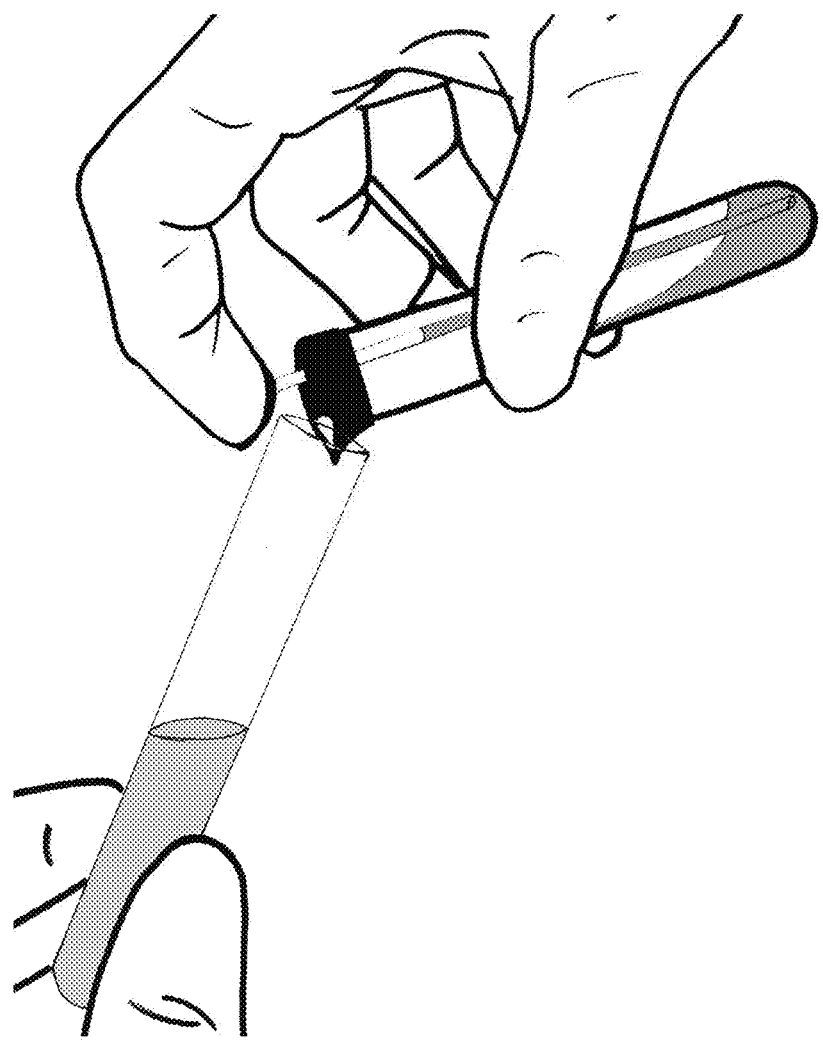
Fig. 6.II

DEVICE FOR STANDARD PREPARATION OF URINARY SEDIMENT FOR URINE ANALYSIS (MONO SYSTEM)

FIELD OF INVENTION

Standardization of the process for preparation and concentration of urinary sediment before microscopic analysis in out-patient and in-patient clinical diagnostic laboratories.

BACKGROUND OF THE INVENTION

Currently performing complete urine analysis in clinical diagnostic laboratories is accompanied by some shortcomings in concentration of the urinary sediment. In spite of development of various systems including Urisystem (by Fisher Scientific) KOVA System (by Hycor Biomedical), and CenSlide 2000 (by StatSpin), there are still some limitations in the test. Therefore there was a need to design a new system that would simplify urine sampling based on the current protocols.

SUMMARY OF THE INVENTION

Current system (Mono System) is comprised of two tubes (inner and main tubes); with one (inner tube) located inside the other. An upper end of inner tube is closed end whereas it has an open lower end. The inner tube has a volume equal to one twelfth ($1/12$) of the main tube, and its wall is attached to and tangential with the wall of the main tube.

An aperture is located at a point near the upper end and on the wall of each of inner and main tubes. This single aperture connects the inner tube with the main tube such that air in the thin inner tube is evacuated when urine enters the tube from its open end. Therefore a concentration of one twelfth ($1/12$) of a sample of any specimen (such as urine) with any starting volume is stored in the inner tube.

According to current protocols, after centrifugation of urine sample at 400-450×g for five minutes, the urinary sediment is used for microscopic evaluation after concentration to a standard level. This ratio is considered to be one twelfth in the Mono System according to the routine practice in most diagnostic laboratories. Mono System (FIG. 1I) is comprised of a main tube and a thin inner tube (without capillarity), which is attached to the wall of the main tube and has the volume equal to one twelfth of the main tube.

A lower end of the thin inner tube is open and located very close to the lower end of the main tube. The upper end of the thin inner tube is closed, and is at the same level of the upper edge of the main tube. Near the upper ends of both tubes, there is one aperture on the wall of each tube, such that by attachment of the walls of the two tubes, the openings are connected, and air can come out from the inner tube when urine enters from the tube end (FIG. 1.II). Therefore, when urine is poured into the main tube, the inner tube is filled from its end (following the exit of air from the inner tube through the upper opening) until it reaches the level of urine in the main tube.

After carrying out basic studies, the tube is centrifuged at 400-450×g for five minutes. Before removal of the supernatant liquid (the urine above the precipitate), operator's thumb is pressed against the opening of the main tube (FIG. 1.III), and the tube is turned upside-down and its contents is poured into another tube for further evaluations. Since the upper end of the thin inner tube is closed and the opening of the main tube is blocked, the contents of the thin inner tube (urine at the volume equal to one twelfth of the basic sample) will remain in the system. Then, the tube is returned back to its original position and the thumb is released, which allows the retained urine in the thin inner tube to be added to the sediment in the main tube (FIG. 1.IV). The sediment is resuspended by flicking of the bottom of the tube and the concentrate is used for microscopic evaluation.

The aim of designing this Mono System is standardization of urinary sediment preparation for microscopic urine analysis in clinical diagnostic laboratories. This system allows highly precise concentration of urinary sediment, and hence precise calculation and report of microscopic findings in this sediment.

Advantages of Mono System:

The advantages of the current invention is explained below:

1—Standardization of microscopic urine analysis.

2—Not being limited by the small volume of the urine sample.

In some laboratories, the KOVA system is currently used, by which if the early volume of the urine sample in the tube is exactly 12 ml, the user can keep 1 ml of the urine in the tube (one twelfth of the early volume) for concentration of the sample. If the early sample is less than 12 ml, the system is not effective. Many patients cannot produce the early volume of 12 ml for physiological or pathological reasons. To alleviate this shortcoming, many books suggest using 3 ml as the starting volume. After centrifugation and pouring out the supernatant, the remaining drop in the tube is almost equal to one twelfth of the starting volume. However, there is a considerable inter-sample variation in this method. On the other hand, when the initial urine volume is less than 2 ml, carrying out centrifugation step is not recommended because of high error rate. Mono System does not have any limitations in this respect and the user can perform the standard concentration step with any starting urine volume.

3—Ease of concentration.

In systems such as the KOVA System, to maintain 1 ml of the urine sample at the bottom of the tube, the user has to use another tool (the user inserts the tool in a tube full of urine and then turns the tube upside-down. The system always keeps 1 ml of the urine sample at the end of the tube). In the Mono System, no other tools are required and the user may keep one twelfth of the early volume only by pressing the thumb against the upper opening of the tube.

4—No need for control of the starting volume and thus, saving the time.

In systems such as the KOVA System, the user has to always use 12 ml urine sample. Thus, graduated tubes are used in the system, and when the urine is poured from the collecting container into the tube, the process should be performed carefully. This is while in the Mono System, it is not required to use graduated tube, and without determining the volume needed, only a random volume of the urine sample is poured into the tube and then the sample is centrifuged. Thus, a considerable amount of time, and energy is saved.

BRIEF DESCRIPTION OF THE DRAWINGS

FIG. 1.I. is a schematic drawing of Mono System and its components; a main tube, b round distal end, c aperture (small opening) for connection of inner tube d with outside environment, e distal opening of the inner tube B, f proximal end of the inner tube d, g proximal opening of main tube a.

FIG. 1.II. displays Mono System when filled from the collecting container.

FIG. 1.III. displays Mono System when turned upside-down after centrifugation.

FIG. 1.IV. displays return of one twelfth of the urine sample volume from the thin inner tube on the sediment inside the main tube.

FIG. 3. Displays a schematic view of Mono System with a flat base.

FIG. 4. Displays a schematic view of Mono System with a long tip.

FIG. 5. Displays a schematic view of Mono System with inner tube which is molded together with the main tube.

FIG. 6.I. displays a schematic view of modified Mono System and its components:

Figure 2:
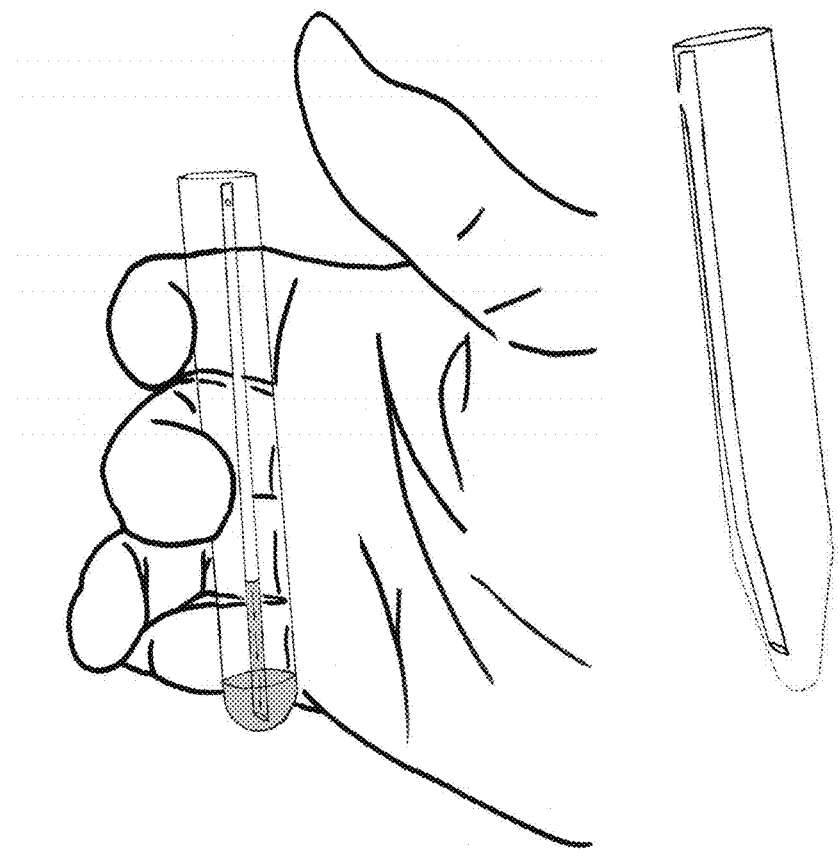
FIG. 2. Is a schematic view of Mono System with a conical base.

screwed lid or cap 30, elongated tip 10 on the lid 30, internal/inner tube 40 with proximal open end embedded in lid 30 and its distal end opening is placed inside main tube 20, main screw-lidded tube 20 with round (or conical or flat) base.

FIG. 6.II. displays a modified Mono System when turned upside-down after centrifugation.

DESCRIPTION OF THE REFERRED EMBODIMENTS

Mono system is comprised of a main tube a comprising of differently-shaped bases such as a round base; a conical base and a flat base. Main tube a comprises an upper end that could be either tipped and/or plain.

Main tube a can contain different volumes of urine including but not limited to 3 ml, 12 ml, 15 ml and 30 ml or more.

An inner surface of wall of main tube a is in contact with a thin inner tube d, which is completely tangential with main tube a. Inner tube d could be designed differently including but not limited to fabricated separately and attached to the inner surface of the main tube a, or it can be molded together with the main tube a.

Inner tube's volume is a fraction of the main tube's volume including but not limited to one fifth, on twelfth, one twentieth or more.

The inner tube d does not have the capillarity property. The two tubes have uniform cross-sections from top to bottom. A small aperture c connects then two tubes together at one point which comprises different diameters including but not limited to 0.5 mm, 2 mm, 5 mm or as needed fit for such utilization of such tube in the art Aperture c is located near an upper end (proximal opening of main tube a as shown in figures below) of the main tube a, which connects the inner space of the inner tube d with the outside environment.

If the two tubes are separately designed and attached, appropriate insulation should be performed around the opening c to avoid any leakage. The two tubes should be made of the same material in order to produce the same surface tension at the interface with the urine sample in the two tubes.

In other preferred embodiments (FIGS. 6.I and 6.II) main tube 20 comprises a cap/lid 30 which could be screwed to main tube 20 in order to prevent spillage of urine during handling of the specimens or having a spout 10 to ease pouring out of the urine from the sample without opening the main tube.

The inner tube 40 could be attached to the inside wall of main tube 20, or inserted into the cap 30, were its proximal open end points out form the cap and is open (the user places its thumb or index finger on this end).

In this new embodiment, the cap/lid 30 is removed in order to use the Mono System, and then the main tube 20 is filled with the required volume of urine. Then, the lid/cap 30 is screwed back on the main tube 20. The main tube 20 is centrifuged according to the instructions. Then, an index finger is placed on the upper end (proximal open end) of the inner tube 40 in order to block it (FIG. 6.II) to maintain a specific amount of urine ($\frac{1}{12}^{th}$ of the total volume stored in main tube 20) and therefore creating a suction force at the proximal end. While tightly holding the proximal end of inner tube 40, the urine in the main tube 20 is poured out (through an elongated end/spout 10) and then main tube 20 is returned back to its normal position by tilting it upright. At this moment, the index finger is removed from the upper end of the inner tube 40. The urine trapped inside the inner tube 40 is now released inside the main tube 20. This will allow one-twelfth of the original volume of urine to be mixed with the depositions. For a better result main tube 20 should be shaken to properly mix the urine and the deposition. The result could be used for microscopic examination.

The Mono System could be made from different materials including but not limited to glass, any transparent plastic, any opaque plastic. However, a hydrophobic material is preferred from complete evacuation of the urine sample. Moreover, considering the difficulty of washing the inner tube, the Mono System should be designed as a disposable system. It should be noted that, in the modified Mono System, the inner tube d could be dismantled from the main tube a and could be washed and sterilized. This will allow multiple uses of this system.

Mono System would find a special place in clinical laboratories, as well as health care centers and hospitals in standardization of preparation of urinary sediment for microscopic analysis. Therefore, the Mono System should be made from material which can be easily disposed with routine methods. Since the appearance of the Mono system can be modified to be more easily used, it can be mentioned that the innovation is not limited to the prototype described above.

As displayed in the drawings the main tube and inner tube comprise different configurations and designs. However it is obvious that other designs and configurations may be used for taking and analyzing bodily fluids, such as urine samples.

The invention claimed is:

1. A Mono System for urine sediment analysis comprising: a main tube comprising a closed distal end and an open proximal end, having a main volume; an inner tube, located inside said main tube comprising an open distal end and a closed proximal end; wherein each of said inner and main tube consist of a small aperture/opening, located on a side wall and next to said proximal end of each of said inner and main tubes respectively, wherein an inside wall of said main tube around said small aperture of said main tube is connected and attached to an outer wall of said small aperture of said inner tube, creating a tightly sealed connecting point; wherein outside air or liquid can only travel directly through said small aperture of said inner tube, and through said inner tube and exit via said open proximal end of said inner tube or vice versa; said inner tube has a maximum volume of at least one-twelfth of said main volume; and said main tube and said inner tube are parallel through their respective axis and wherein said open proximal end of said inner tube is straight and stands away from said closed proximal end of said main tube, allowing enough room for urine sediment analysis without disturbing or contacting any sediment located at said closed distal end of said main tube; wherein when a fluid sample is poured inside said main tube said small aperture of both of said inner and main tube at said connecting point is blocked from outside air via an index finger and therefore trapping a small fluid sample inside said inner tube; wherein when said fluid sample is discarded from said main tube, said outside air is allowed to travel inside said inner tube through said small aperture of said inner tube by removing said index finger and therefore mixing said small fluid sample with said sediment at a bottom of said closed distal end of said main tube.

2. The Mono System of claim 1, wherein said closed distal end of said main tube comprises a round, conical shape or flat shape, providing enough space for said small fluid sample to mix with said sediment.

3. The Mono System of claim 2, wherein said small apertures of said main and said inner tubes respectively is located closer to said proximal ends of each of said tubes rather than said distal ends of each of said tubes respectively.

4. The Mono System of claim 3, wherein said inner tube has a very thin diameter in comparison to a diameter of said main tube.

5. The Mono System of claim 4, wherein an air inside said inner tube exits through said small aperture of said inner tube and main tube to outside, at said connecting point and no air or liquid leaks at said connecting point.

6. The Mono System of claim 5, wherein both of said main and inner tubes comprise a uniform cross-section from top to bottom when taken coaxially.

7. The Mono System of claim 6, wherein both of said main and inner tubes are unitarily formed from a transparent plastic, opaque plastic and/or glass.

8. The Mono System of claim 7, wherein said aperture comprises a diameter of 0.5 to 5 mm.

9. The Mono System of claim 8, wherein said aperture comprises a diameter of 1 mm.

10. The Mono System of claim 8, wherein said main volume is in a range of 3 to 30 ml.

11. The Mono System of claim 10, wherein said main volume is in a range of 12 ml.

12. The Mono System of claim 10, wherein said main tube comprises a spout at its open proximal end facing away from said small aperture of said main tube.

13. The Mono system of claim 8, wherein said open proximal end of said main tube comprises a screwed on top cap/lid therefore preventing spillage of said fluid sample.

14. The Mono system of claim 13, wherein said cap/lid comprises a spout and an opening allowing discard of said fluid sample.

15. The Mono system of claim 14, wherein said inner and main tubes are graded and comprise markers and numbers.

* * * * *